United States Patent [19]
Andrews et al.

[11] Patent Number: 4,631,082
[45] Date of Patent: Dec. 23, 1986

[54] COBALT-CHROMIUM SUPERALLOY

[75] Inventors: Henry L. Andrews, Old Saybrook; Gregory E. Gardiner, Branford, both of Conn.

[73] Assignee: Pfizer Hospital Products Group Inc., New York, N.Y.

[21] Appl. No.: 703,352

[22] Filed: Feb. 20, 1985

[51] Int. Cl.$^4$ ............................................. C22C 29/12
[52] U.S. Cl. ........................................ 75/235; 75/232; 420/438; 148/408
[58] Field of Search ............... 75/232, 235; 419/32, 419/33, 41, 50; 420/436, 438; 148/408

[56] References Cited

U.S. PATENT DOCUMENTS

| | | |
|---|---|---|
| 3,591,362 | 7/1971 | Benjamin ............ 75/235 |
| 3,728,088 | 8/1969 | Benjamin ............ 75/235 |
| 3,749,612 | 4/1971 | Benjamin et al. ...... 75/235 |

FOREIGN PATENT DOCUMENTS

| | | | |
|---|---|---|---|
| 3943 | 1/1983 | Japan ............ | 420/438 |
| 974185 | 11/1964 | United Kingdom ... | 420/438 |

OTHER PUBLICATIONS

John S. Benjamin, "Dispersion Strengthened Superalloys by Mechanical Alloying", Metallurgical Transactions, vol. 1, Oct. 1970, p. 2943.

Primary Examiner—Stephen J. Lechert, Jr.
Assistant Examiner—Anne Brookes
Attorney, Agent, or Firm—Charles J. Knuth; Peter C. Richardson; Mark Dryer

[57] ABSTRACT

An oxide dispersion strengthened cobalt-chromium superalloy produced by mechanical alloying containing a refractory oxide, preferably yttrium oxide, and characterized by excellent corrosion resistance, high fatigue strength and high temperature stability; and prostheses formed from said superalloy.

5 Claims, 2 Drawing Figures

COBALT-CHROMIUM SUPERALLOY

BACKGROUND OF THE INVENTION

This invention relates to a cobalt-based alloy containing a substantial proportion of chromium and referred to herein as a cobalt-chromium superalloy. More particularly the invention is concerned with certain cobalt-chromium oxide dispersion strengthened (O.D.S.) superalloys produced by a mechanical alloying process.

The term "superalloy" is a term of art which generally signifies an alloy having particularly high strength, good mechanical and corrosion-resistant characteristics and a stable microstructure. Of particular interest are those alloys which additionally retain high strength properties (and stable microstructures) following thermal treatments at extremely high temperatures.

The known alloy Vitallium ® is a high corrosion-resistant cobalt/chromium alloy which is used successfully in numerous orthopaedic applications. A typical composition for Vitallium is the following:

| Element | % by weight |
|---|---|
| Carbon | 0.25 |
| Silicon | 0.75 |
| Manganese | 0.70 |
| Chromium | 28.00 |
| Molybdenum | 5.50 |
| Cobalt | 64.80 |

Because of its many favorable properties, particularly corrosion resistance, Vitallium is used extensively in orthopaedic applications, especially for prostheses. A particularly useful development in the area of orthopaedic implants is the provision of a porous coating in the form of multiple layers of spherical Vitallium particles on the surface of a Vitallium implant to encourage bone-growth in a cementless system.

It is known that the properties of a given metal alloy are dependent upon its composition and also upon the manner in which the various alloying ingredients are formed into the final alloy. "Mechanical alloying" is a process which produces homogeneous composite particles with an intimately dispersed, uniform internal structure. The process is described in an article entitled "Dispersion Strengthened Superalloys by Mechanical Alloying" by John S. Benjamin, Metallurgical Transactions, Vol. 1, October 1970, p. 2943.

U.S. Pat. No. 3,591,362, issued July 6, 1971 to John S. Benjamin discloses a composite metal powder formed by the technique of mechanical alloying.

Mechanical alloying is particularly advantageous for making superalloys that cannot be made readily by melting or by conventional powder metallurgy. Since the strength, and certain other properties, of superalloys depends ultimately on the presence of dispersions of intermetallic compounds and the utility of the superalloy is inherently limited by the stability of these components, the choice of dispersant materials, as well as alloying metals, is important for the performance of the final alloy.

It is known that the inclusion of certain selected oxides in the alloy composition can improve the properties of the final alloy and oxide dispersion strengthened (O.D.S.) superalloys made by the mechanical alloying process exhibit high-temperature strength and stability as a result of the presence of stable oxide dispersions which resist thermal damage and permit much greater freedom in alloy design.

It has now been found that improved cobalt-chromium superalloys made in accordance with O.D.S. mechanical alloying procedures not only have the high corrosion-resistant properties typical of Vitallium but also have excellent room temperature strength (tensile and fatigue) properties which are substantially retained after exposure to severe thermal conditions. These properties are substantially more advantageous than would be expected from prior art alloys made by similar techniques, for example the nickel-chromium, cobalt-chromium (of different composition to those specified herein), and iron-chromium systems disclosed in U.S. Pat. No. 3,591,362.

SUMMARY OF THE INVENTION

In accordance with the present invention there is provided a high strength, corrosion-resistant, high temperature stable, composite alloy produced by mechanical alloying and consisting essentially of the following percentage composition by weight:

| | |
|---|---|
| chromium | 26 to 30 |
| molybdenum | 5 to 7 |
| manganese | 0 to 1 |
| silicon | 0 to 1 |
| iron | 0 to 1.5 |
| nickel | 0 to 2.5 |
| carbon | 0 to 0.35 |
| refractory oxide | 0.05 to 1.0 |
| aluminum | 0.05 to 0.6 |
| titanium | 0.05 to 0.6 | and the balance cobalt, apart from trace amounts of incidental impurities; in which the refractory oxide is silica or an oxide of a metal of Group IIA, IIIA, IIB or IVB of the Periodic Table which forms high temperature-stable, non-accretive, fine particles and is present in the dispersed phase, and said alloy, after fabrication by mechanical alloying, consolidation and hot rolling, has an ultimate tensile strength of at least 250, preferably 280 to 300 k.s.i. (p.s.i.$\times 10^3$), a 0.2% offset yield strength of at least 220, preferably 235 to 275 k.s.i., an elongation of 2 to 5%, and a fatigue strength at $10^7$ cycles (Rotating Cantilever Beam) of at least 100 k.s.i.

The refractory oxide which provides the dispersed oxide phase in the improved ODS superalloy of the invention is suitably an oxide of a metal whose negative free energy of formation of the oxide per gram atom of oxygen at about 25° C. is at least about 90,000 calories and whose melting point is at least about 1300° C. Additionally the oxide must be adapted to form non-accretive fine particles in the dispersed phase. Examples of suitable refractory oxides are the oxides of silicon, beryllium, magnesium, calcium, aluminum, yttrium, cerium, titanium, zirconium, hafnium and thorium.

The most preferred oxide for the purposes of the present invention and particularly when the superalloy is used for the production of prostheses, is yttrium oxide, $Y_2O_3$; and the invention will be particularly described herein with reference to this preferred oxide.

A preferred embodiment of the invention is a high strength, corrosion-resistant, high temperature stable, composite alloy as described above in which the percentage composition by weight is:

| | |
|---|---|
| chromium | 26.20 |
| molybdenum | 5.40 |

-continued

|  |  |
|---|---|
| manganese | 0.78 |
| silicon | 0.67 |
| iron | 0.18 |
| nickel | 0.45 |
| carbon | 0.025 |
| yttrium oxide ($Y_2O_3$) | 0.50 |
| aluminum | 0.59 |
| titanium | 0.30 | and the balance cobalt, apart from trace amounts of incidental impurities.

Another preferred embodiment is an alloy as described above in which the percentage composition by weight is:

|  |  |
|---|---|
| chromium | 26.00 |
| molybdenum | 5.20 |
| manganese | 0.79 |
| silicon | 0.76 |
| iron | 0.17 |
| nickel | 0.56 |
| carbon | 0.03 |
| yttrium oxide | 0.54 |
| aluminum | 0.27 |
| titanium | 0.30 | and the balance cobalt, apart from trace amounts of incidental impurities.

The invention also provides a prosthethic device formed from an alloy as described. Preferably the alloy is forged into the required shape for the prosthetic device, for example, an artificial hip.

DETAILED DESCRIPTION OF THE INVENTION

The high strength, corrosion-resistant, high temperature stable, composite alloy of the invention is produced in powder form by mechanical alloying, which comprises subjecting a mixture of the metallic and oxide ingredients to dry, high energy milling in a grinding mill and continuing the milling under controlled conditions until a uniform distribution of oxide and metallic ingredients is achieved. The resulting homogeneous composite alloy in powder form is then consolidated, preferably by hot extrusion, and the resulting extruded solid alloy is further fabricated by hot rolling.

Mechanical alloying is a dry, high-energy milling process that produces composite metal powders with controlled, extremely fine microstructures. The powder is produced in high-energy attrition mills or special large ball mills. For the production of the ODS alloy according to the present invention, a mixture of commercially available metal powders, master alloy alloy powders and the very fine oxide powder is charged into the grinding mill.

Under controlled conditions powder particles first cold weld together, building up larger particles and then fracture, breaking down into the composite powder particle. The interplay between the welding and fracturing subdivides and kneads all the ingredients to provide a very uniform distribution of the oxide and the metallic components.

The resulting oxide-containing powder is consolidated by extrusion and hot rolling prior to forging into the desired configuration for a prosthesis. Consolidation techniques other than extrusion, for example hot isostatic pressing or rapid omnidirectional compaction (ROC) (see U.S. Pat. No. 4,142,888) may be used.

BRIEF DESCRIPTION OF DRAWINGS

The invention is more particularly described with reference to the accompanying drawings in which:

Referring to FIG. 1 of the drawings, this clearly illustrates that a superalloy piece made from a typical mixture of alloying ingredients according to the invention and fabricated by the mechanical alloying, extrusion and hot-rolling steps described herein rivals the strength levels of the ultra-high strength steels which have, as a family, the highest strength levels of any industrial alloy systems.

The $10^7$ cycle rotating beam fatigue strengths for these ultra-high strength steels ranges from 105,000 to 135,000 psi. The ODS superalloy of the invention as-hot rolled far surpasses these materials with a $10^7$ cycle value of 157,000 psi. Even the full sinter cycle annealed material is very competitive at 107,000 psi.

Figure 1:
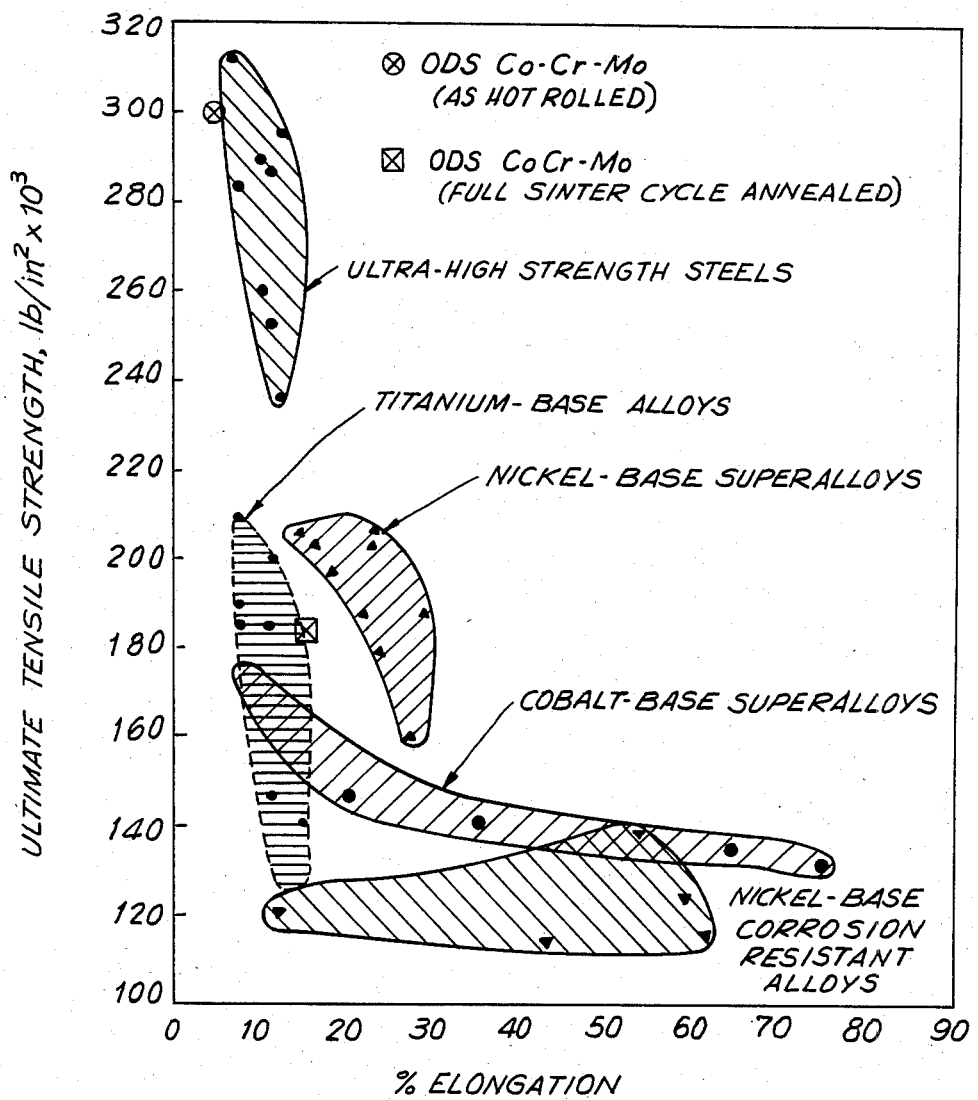
FIG. 1 is a graph illustrating the relationship between tensile strength and percentage elongation for wrought high performance alloys.

These very high strength levels far surpass anything ever observed for wrought cobalt-base superalloys, as illustrated in FIG. 1. In fact, even the full sinter cycle annealed material has strength levels that exceed the solution heat treated and aged properties.

The bar stock resulting from hot rolling may be heat treated, forged to the desired prosthesis shape and then machined to produce a finished smooth surface prosthesis.

If desired, the smooth surface prosthesis then may be further treated to provide a porous coated prosthesis.

Figure 2:
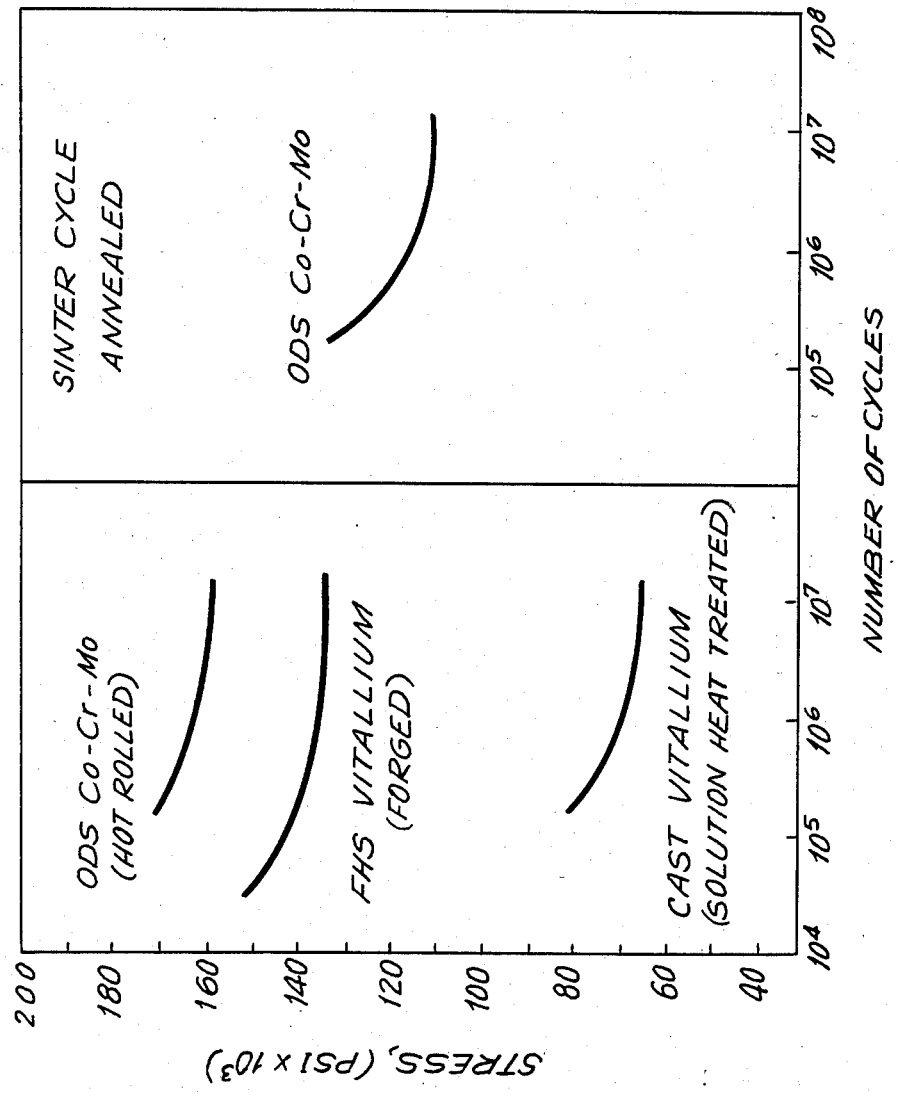
FIG. 2 is a combination of two graphs illustrating a comparison between fatigue properties of a preferred alloy according to the invention and those of FHS Vitallium and cast Vitallium.

In FIG. 2 of the drawings the fatigue properties of a preferred alloy of the invention as illustrated in Example 1 are compared in the first graph with the fatigue properties of FHS Vitallium and cast Vitallium, respectively. The second graph shows that the alloy of the invention retains a fatigue strength comparable to that of FHS Vitallium even after thermal exposure.

The following Examples illustrate the invention and the manner in which it may be performed.

EXAMPLE 1

A mixture of alloying ingredients comprising in percentage by weight:

|  |  |
|---|---|
| chromium | 26.20 |
| molybdenum | 5.40 |
| manganese | 0.78 |
| silicon | 0.67 |
| iron | 0.18 |
| nickel | 0.45 |
| carbon | 0.02 |
| ytrrium oxide | 0.50 |
| aluminum | 0.59 |
| titanium | 0.30 |
| cobalt | balance | was introduced into a grinding mill or attritor of the stirred ball mill type capable of providing agitation milling or high energy milling. This is a condition wherein sufficient mechanical energy is applied to the total charge so that a substantial portion of the attritive elements are continuously maintained in a state of relative motion. This type of milling is described in U.S. Pat. No. 3,591,362.

The high energy milling in air was continued for about 24 hours until a substantially homogeneous powder of the oxide-containing superalloy was produced.

The said superalloy powder was passed from the attritor into an extrusion can and then to an extrusion press where it was consolidated into an extrusion billet of about 4 inches diameter.

The billet emerging from the extrusion press was then hot rolled to a rod of about 1 inch diameter.

The as-hot rolled one inch diameter rod was subjected to the Krouse Cantilever rotating beam fatigue test and the resulting data are given in the first graph of FIG. 2.

The rod was then given a full sinter cycle anneal.

The fatigue properties of the superalloy subjected to the full sinter cycle anneal are illustrated in the second graph of FIG. 2.

The as-hot rolled superalloy prepared above had a tensile strength of 299 k.s.i.; a 2% offset yield strength of 259 k.s.i.; and a room temperature ductility (elongation) of 4.4%.

The full sinter cycle annealed alloy had a tensile strength of 184 k.s.i.; a 2% offset yield strength of 150 k.s.i. and a ductility of 14.5%.

EXAMPLE 2

A mixture of alloying ingredients comprising in percentage by weight

| chromium | 26.00 |
| --- | --- |
| molybdenum | 5.20 |
| manganese | 0.79 |
| silicon | 0.76 |
| iron | 0.17 |
| nickel | 0.56 |
| carbon | 0.03 |
| yttrium oxide | 0.54 |
| aluminum | 0.27 |
| titanium | 0.30 |
| cobalt | balance | was processed in a similar manner to the mixture in Example 1. The resulting alloy powder was consolidated, hot-rolled and subjected to the same heat treatment steps as the alloy of Example 1 and the tensile properties of the resulting alloy were comparable to those of the alloy of Example 1.

The alloys of both Examples 1 and 2 above are biocompatible and are particularly suitable for use in prostheses. Both comply with ASTM F799-82, "Standard Specification for Thermodynamically Processed Cobalt-Chromium-Molybdenum Alloy for Surgical Implants" which permits 1.0% maximum nickel and 1.5% maximum iron.

The chemistry of the ODS superalloy of the invention is unique. Compared to FHS Vitallium ® the superalloy of the invention has the specific alloying additions of yttrium oxide, aluminum and titanium which accomplish the desired purpose of retaining substantially high values of the tensile and fatigue strengths following thermal exposure.

This alloy chemistry accomplishes the above by forming a combined dispersion ($Y_2O_3$-$Al_2O_3$) that, because of a close interparticle spacing, prevents significant growth in grain size and avoids resulting loss of properties.

This unique cobalt-base alloy chemistry is particularly adapted for the specific application of porous coated prostheses that provide a new improved method of prosthesis fixation eliminating the use of bone cement.

We claim:

1. A high strength, corrosion-resistant, high temperature stable, consolidated, biocompatible, composite alloy produced by mechanical alloying and consisting essentially of the following percentage composition by weight:

| chromium | 26 to 30 |
| --- | --- |
| molybdenum | 5 to 7 |
| manganese | 0 to 1 |
| silicon | 0 to 1 |
| iron | 0 to 1.5 |
| nickel | 0 to 2.5 |
| carbon | 0 to 0.35 |
| refractory oxide | 0.05 to 1.0 |
| aluminum | 0.05 to 0.6 |
| titanium | 0.05 to 0.6 | and the balance cobalt, apart from trace amounts of incidental impurities; in which the refractory oxide is silica or an oxide of a metal of Group IIA, IIIA, IIIB or IVB of the Periodic Table which forms high temperature-stable, non-accretive, fine particles and is present in the dispersed phase and said alloy after fabrication by mechanical alloying, consolidation and hot rolling, has an ultimate tensile strength of at least 250 k.s.i., a 0.2% offset yield strength of at least 220 k.s.i., an elongation of 2 to 5%, and a fatigue strength at $10^7$ cycles (Rotating Cantilever Beam) of at least 100 k.s.i.

2. An alloy according to claim 1, in which the refractory oxide is yttrium oxide, $Y_2O_3$.

3. An alloy according to claim 2, in which the percentage composition by weight is:

| chromium | 26.20 |
| --- | --- |
| molybdenum | 5.40 |
| manganese | 0.78 |
| silicon | 0.67 |
| iron | 0.18 |
| nickel | 0.45 |
| carbon | 0.02 |
| yttrium oxide | 0.50 |
| aluminum | 0.59 |
| titanium | 0.30 | and the balance cobalt, apart from trace amounts of incidental impurities.

4. An alloy according to claim 2 in which the percentage composition by weight is:

| chromium | 26.00 |
| --- | --- |
| molybdenum | 5.20 |
| manganese | 0.79 |
| silicon | 0.76 |
| iron | 0.17 |
| nickel | 0.56 |
| carbon | 0.03 |
| yttrium oxide | 0.54 |
| aluminum | 0.27 |
| titanium | 0.30 | and the balance cobalt, apart from trace amounts of incidental impurities.

5. An alloy according to claim 2, in which said fabrication comprises the steps of: (1) mechanical alloying by subjecting a mixture of the metallic and oxide ingredients to dry, high-energy milling in a grinding mill and continuing the milling until a uniform distribution of oxide and metallic ingredients is achieved; (2) consolidating the resulting homogeneous composite alloy in powder form by hot extrusion, and (3) hot rolling the resulting extruded solid alloy.

* * * * *